US012508135B2

(12) United States Patent
Rivera, Jr.

(10) Patent No.: US 12,508,135 B2
(45) Date of Patent: Dec. 30, 2025

(54) ENHANCED IMPLANT REMOVAL TOOL CONNECTION INTERFACE

(71) Applicant: DePuy Ireland Unlimited Company, Ringaskiddy (IE)

(72) Inventor: Jose S. Rivera, Jr., Naples, FL (US)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 214 days.

(21) Appl. No.: 18/374,737

(22) Filed: Sep. 29, 2023

(65) Prior Publication Data

US 2024/0108475 A1 Apr. 4, 2024

Related U.S. Application Data

(60) Provisional application No. 63/411,417, filed on Sep. 29, 2022.

(51) Int. Cl.
*A61F 2/46* (2006.01)

(52) U.S. Cl.
CPC .... *A61F 2/4603* (2013.01); *A61F 2002/4619* (2013.01); *A61F 2002/4627* (2013.01)

(58) Field of Classification Search
CPC ............ A61F 2/4603; A61F 2002/4619; A61F 2002/4627
USPC ........................................ 606/99–100, 79–86
See application file for complete search history.

(56) References Cited

U.S. PATENT DOCUMENTS 4,736,738 A * 4/1988 Lipovsek ........ A61B 17/320016 606/88
4,834,081 A * 5/1989 Van Zile ................. A61F 2/461 606/99
4,919,153 A * 4/1990 Chin ...................... A61F 2/4607 606/100
4,921,493 A * 5/1990 Webb, Jr. ........... A61B 17/1659 606/85
5,409,492 A * 4/1995 Jones ........................ A61F 2/36 606/86 R
5,499,986 A * 3/1996 Dimarco .............. A61B 17/921 606/104
5,690,636 A * 11/1997 Wildgoose ......... A61B 17/1735 606/88
5,788,701 A * 8/1998 McCue .............. A61B 17/1604 606/88
6,790,211 B1 * 9/2004 McPherson ........... A61F 2/4607 606/169
7,296,804 B2 * 11/2007 Lechot ............... A61B 17/1666 279/81

(Continued)

*Primary Examiner* — Jessica Weiss
(74) *Attorney, Agent, or Firm* — XSENSUS LLP

(57) ABSTRACT

In some implementations, a connection interface assembly may include a handle, a connection interface, a locking mechanism, and an implant removal tool. The handle may include a proximal end, a distal end, and a cavity including an interior surface. The distal end may define a distal end opening that is in communication with the cavity. The locking mechanism may be disposed within the cavity of the handle and may be movable between a projected position and a retracted position. The implant removal tool may include a first end and a second end. The second end may form a locking interface element. The implant removal tool may be selectively engageable with the connection interface via an engagement and disengagement between the locking mechanism and the locking interface element.

20 Claims, 8 Drawing Sheets

(56) References Cited

U.S. PATENT DOCUMENTS

| | | | | |
|---|---|---|---|---|
| 9,504,578 | B2 * | 11/2016 | Hood | A61B 17/164 |
| 11,191,651 | B1 * | 12/2021 | Rivera, Jr. | A61F 2/4607 |
| 2003/0083668 | A1 * | 5/2003 | Rogers | A61B 17/92 606/100 |
| 2010/0069909 | A1 * | 3/2010 | Taylor | A61F 2/4607 606/82 |
| 2018/0206859 | A1 * | 7/2018 | Pendleton | A61B 17/1637 |

* cited by examiner

ENHANCED IMPLANT REMOVAL TOOL CONNECTION INTERFACE

CROSS-REFERENCE TO RELATED APPLICATIONS

This application claims the benefit of U.S. Provisional Application No. 63/411,417, filed Sep. 29, 2022, which is incorporated herein by reference in its entirety.

BACKGROUND

Medical revision surgeries are associated with removing and replacing prosthetic components, such as artificial joints or implants, that have become compromised or that require modification because of various factors. In medical revision procedures, implant removal tools may be used to remove the prosthetic components.

SUMMARY

In one aspect, a connection interface assembly, includes a handle including a proximal end, a distal end, and a cavity including an interior surface, the distal end defining a distal end opening that is communication with the cavity, a connection interface including an open top end opposing a bottom portion, the bottom portion being connected to the handle at the distal end and defining a channel that is in communication with the distal end opening, the connection interface including a sidewall extending from the bottom portion to the open top end, the sidewall defining a sidewall opening, the sidewall including an inner sidewall surface, the inner sidewall surface and the bottom portion defining an interface access region that is accessible via the channel, the open top end, and the sidewall opening, a locking mechanism disposed within the cavity of the handle, the locking mechanism being movable between a projected position where the locking mechanism extends into the interface access region and a retracted position where the locking mechanism is retracted from extending into the interface access region, and an implant removal tool including a first end and a second end, the second end forming a locking interface element, the implant removal tool being selectively engageable with the connection interface via an engagement of the locking mechanism with the locking interface element when the locking mechanism is in the projected position and a disengagement of the locking mechanism from the locking interface element when the locking mechanism is in the retracted position.

In one aspect, a method for connecting an implant removal tool to a connection interface coupled to a handle, includes retracting a locking mechanism from an interface access region of the connection interface, inserting a locking interface element of the implant removal tool within the interface access region of the connection interface, and projecting the locking mechanism into the interface access region to engage the locking interface element of the implant removal tool.

In one aspect, a connection interface for connecting a handle to an implant removal tool, includes an open top end opposing a bottom portion, the bottom portion defining a channel configured to be in communication with a cavity of the handle, a sidewall extending from the bottom portion to the open top end, the sidewall including a first inner sidewall surface and a second inner sidewall surface, the first inner sidewall surface defining a first interface access region and a first sidewall opening, having a first width, that provides access to the first interface access region, the second inner sidewall surface defining a second interface access region and a second sidewall opening, having a second width that is narrower than the first width, that provides access to the second interface access region, the first interface access region being configured to receive a first portion of the implant removal tool, the second interface access region being configured to receive a second portion of the implant removal tool, a locking mechanism movable between a projected position where the locking mechanism extends into the first interface access region and a retracted position where the locking mechanism is retracted from extending into the first interface access region, the locking mechanism configured to engage a locking interface element of the first portion of the implant removal tool when the locking mechanism is in the projected position and configured to disengage the locking mechanism from the locking interface element when the locking mechanism moves from the projected position to the retracted position.

DETAILED DESCRIPTION OF EXAMPLE EMBODIMENTS

Figure 1A:
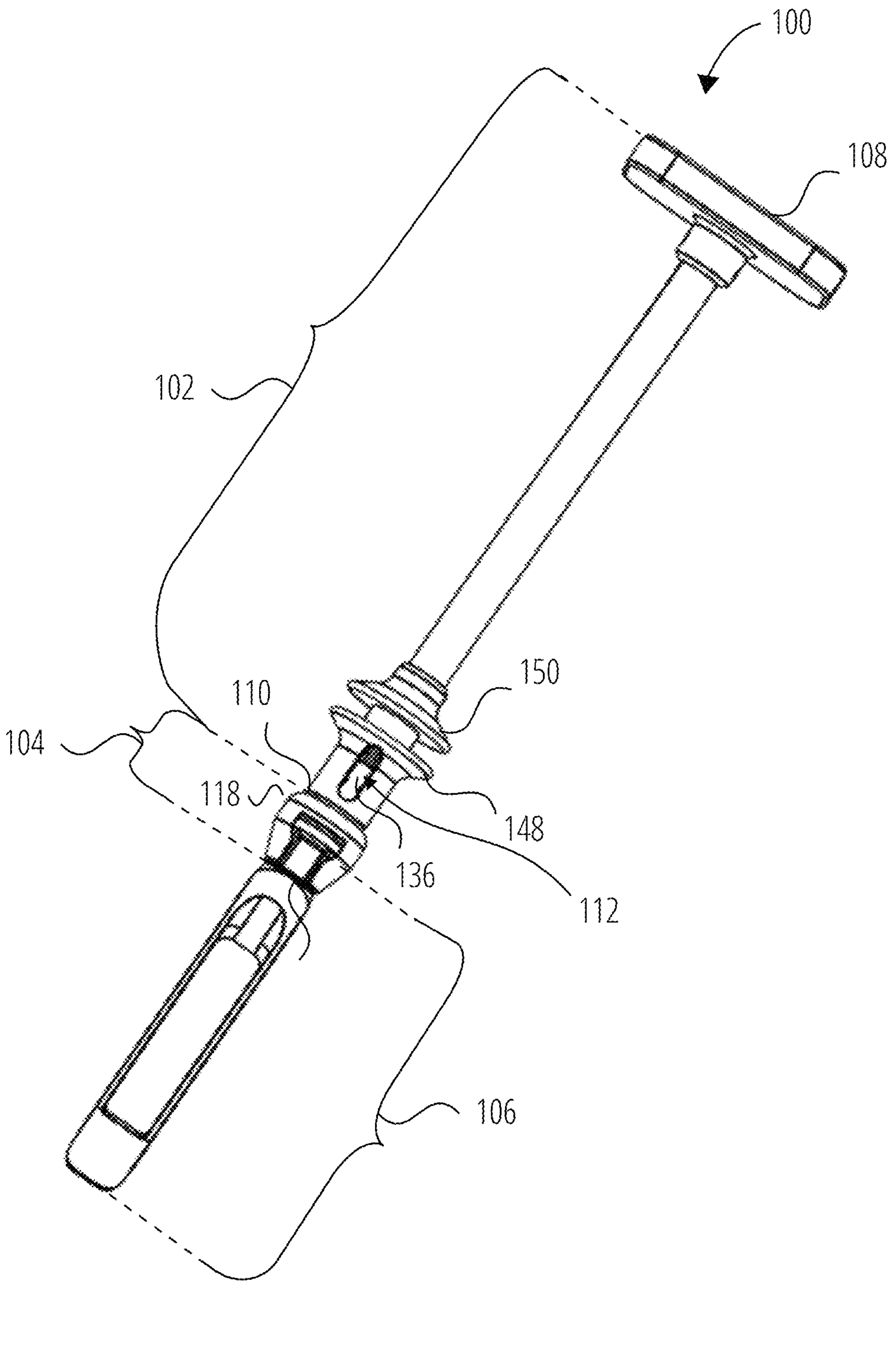
FIG. 1A is a perspective view of an example connection interface assembly in an assembled state, in accordance with some embodiments of the present disclosure.
Figure 1B:
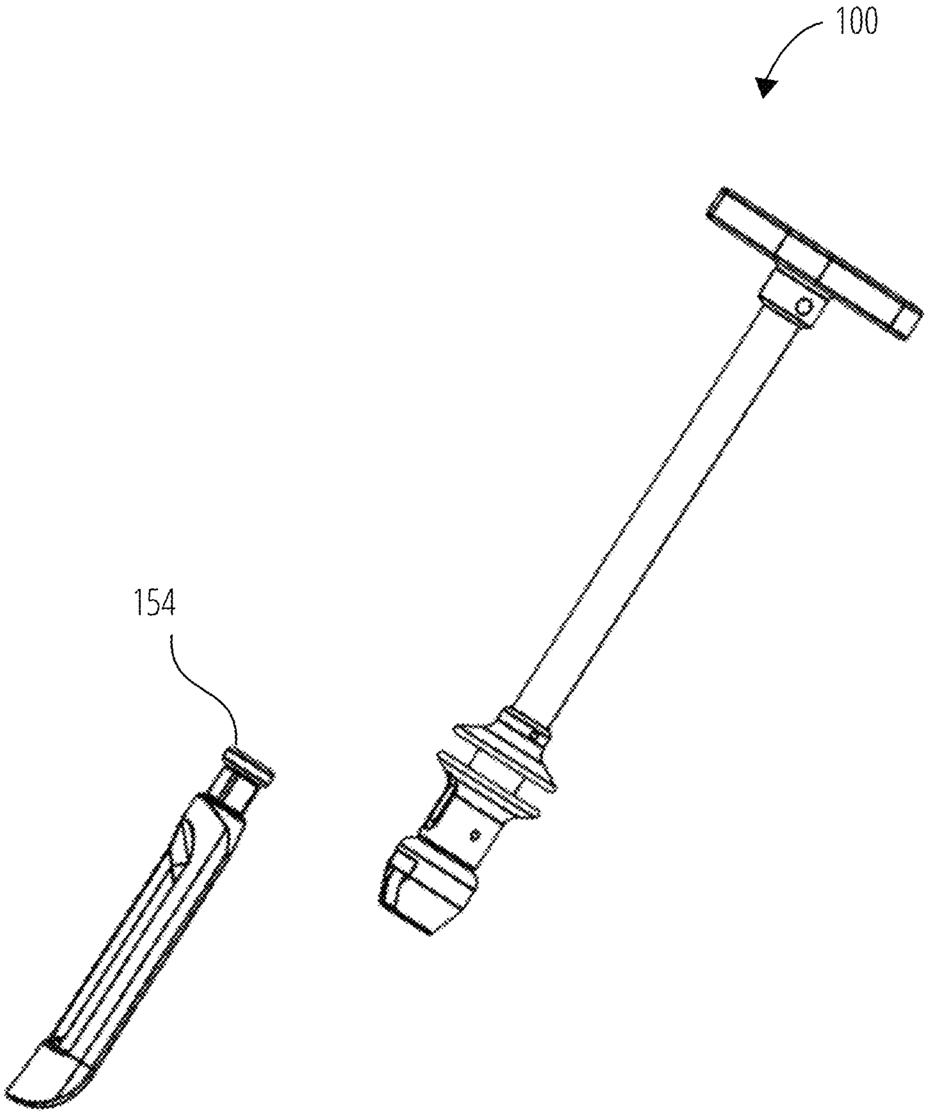
FIG. 1B is a perspective view of an example connection interface assembly where an implant removal tool is separated from a connection interface and a handle, in accordance with some embodiments of the present disclosure.

The following detailed description of example implementations refers to the accompanying drawings. The same reference numbers in different drawings may identify the same or similar elements.

In a medical revision surgery, a surgeon may remove an implant (e.g., a prosthetic implant that is compromised and/or that fails) and may replace the implant with a new or modified implant to address various issues, such as implant-related complications (e.g., infections, loosening of the implants, and/or mechanical failures, among other examples). To perform the medical revision surgery, the surgeon is often required to transition between using various tools (e.g., specialized tools), facilitated by typical connection interface systems, such as screw-on connection interface systems (e.g., where tools are affixed to a handle via a rotational motion that engages complementary threaded portions) and twist-lock connection interface systems (e.g., where tools are secured to a handle via a twisting motion that interlocks complementary components).

However, typical connection interfaces have challenges and drawbacks, including being time-consuming, demanding fine motor skills, risking cross-threading or misalignment, having ergonomic limitations, and the potential for attachment slippage. This hinders surgical efficiency and increases a risk of disruption and/or harm to the medical revision surgery and/or the patient.

Some implementations described herein provide an enhanced connection interface assembly for efficiently and selectively engaging tools (e.g., implant removal tools) to a handle, as described in more detail elsewhere herein. As an example, the connection interface assembly may include a handle, a connection interface, a locking mechanism, and an implant removal tool. The handle may include a proximal end, a distal end, and a cavity. The distal end may define a distal end opening that is in communication with the cavity.

In some implementations, the connection interface may include an open top end opposing a bottom portion. The bottom portion may be connected to the handle at the distal end of the handle. The bottom portion may define a channel that is in communication with the distal end opening. The connection interface may include a sidewall extending from the bottom portion to the open top end. The sidewall may define a sidewall opening and may include an inner sidewall surface. The inner sidewall surface and the bottom portion may define an interface access region that is accessible via the channel, the open top end, and the sidewall opening.

In some implementations, the locking mechanism may be disposed within the cavity of the handle. The locking mechanism may be movable between a projected position (e.g., where the locking mechanism extends into the interface access region) and a retracted position (e.g., where the locking mechanism is retracted from extending into the interface access region).

The implant removal tool may include a first end and a second end, and the second end may form a locking interface element. In some implementations, the implant removal tool may be selectively engageable with the connection interface via an engagement of the locking mechanism with the locking interface element when the locking mechanism is in the projected position and via a disengagement of the locking mechanism from the locking interface element when the locking mechanism is in the retracted position, as described in more detail elsewhere herein.

FIGS. 1A-1J illustrate various views associated with an interface connection assembly 100. As shown in FIG. 1A, the connection interface assembly 100 includes a handle 102, a connection interface 104, and an implant removal tool 106. The handle 102 includes a proximal end 108, a distal end 110, and a cavity 112. The cavity 112 includes a bottom portion 118. The distal end 110 defines a distal end opening 114 that is in communication with the cavity 112.

Figure 1C:
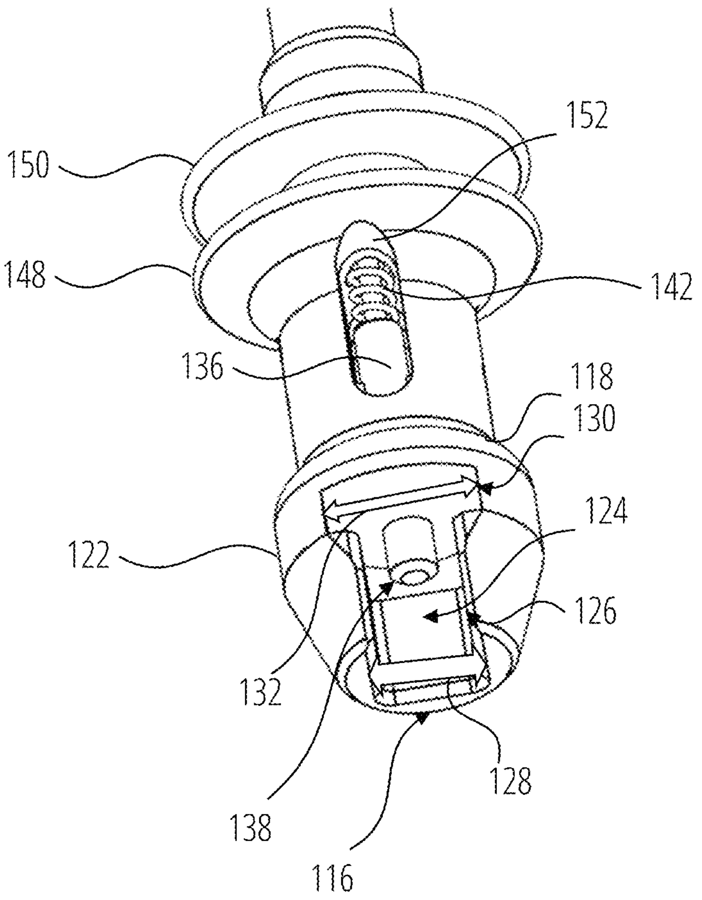
FIG. 1C is a partial perspective view of an example connection interface assembly where a locking mechanism is in a projected position, in accordance with some embodiments of the present disclosure.
Figure 1D:
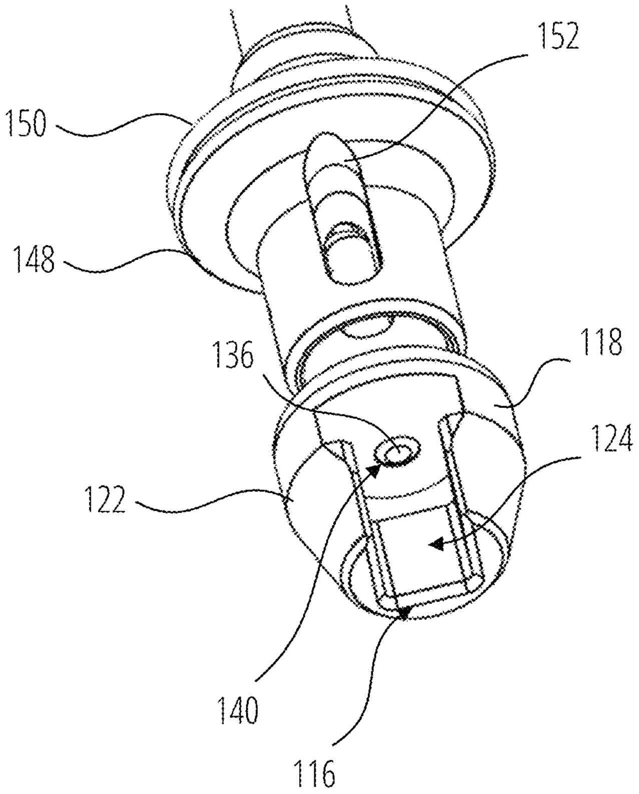
FIG. 1D is a partial perspective view of an example connection interface assembly where a locking mechanism is in a retracted position, in accordance with some embodiments of the present disclosure.
Figure 1E:
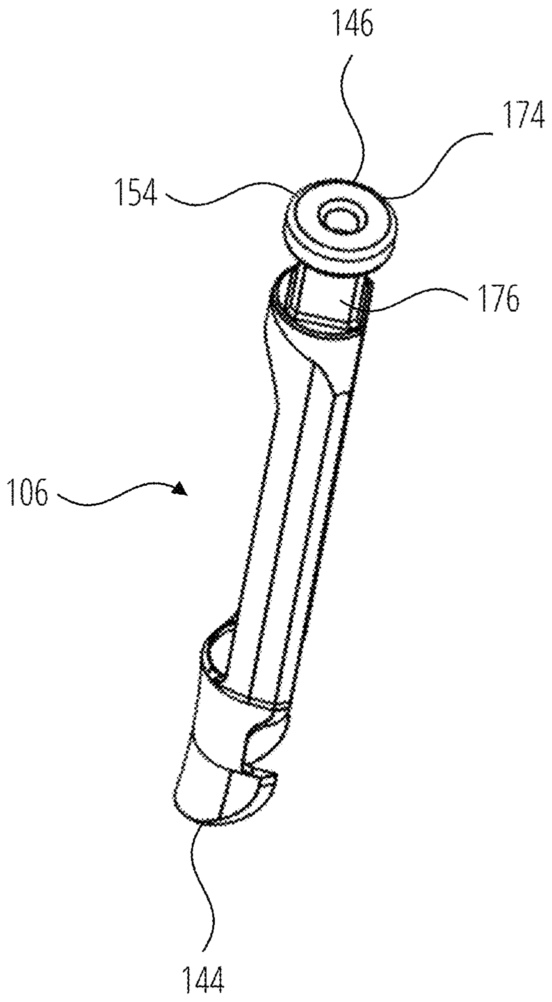
FIG. 1E is a perspective view of an example implant removal tool, in accordance with some embodiments of the present disclosure.
Figure 1F:
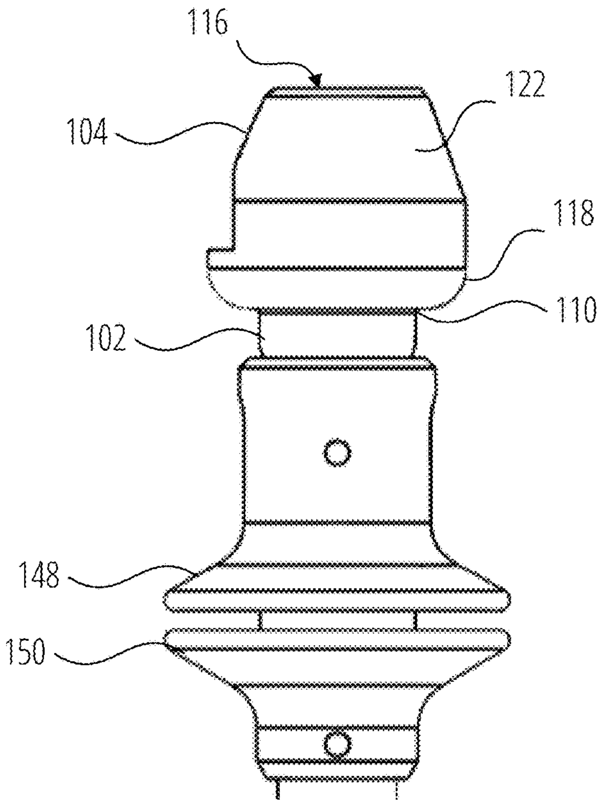
FIG. 1F is a partial side view of an example connection interface assembly including a releasing mechanism proximate to a stopping mechanism, in accordance with some embodiments of the present disclosure.
Figure 1G:
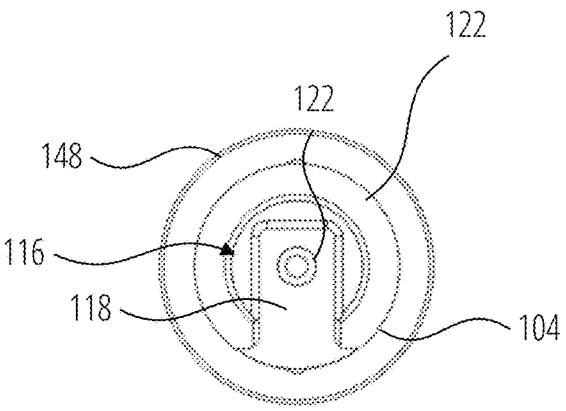
FIG. 1G is a top view of an example connection interface assembly, in accordance with some embodiments of the present disclosure.

The connection interface 104 includes an open top end 116 opposing a bottom portion 118. In some implementations, the open top end 116 may be substantially U-shaped (e.g., when viewed from a top of the connection interface 104 and as shown in FIG. 1G). The bottom portion 118 is connected to the handle 102 at the distal end 110 of the handle 102. The bottom portion 118 defines channel 120 that is in communication with the distal end opening 114.

The connection interface 104 includes a sidewall 122 that extends from the bottom portion 118 to the open top end 116. The sidewall 122 defines a sidewall opening 124 including a top 126 having a first width 128 and a bottom 130 having a second width 132 that is greater than the first width 128. The sidewall 122 and the bottom portion 118 define an interface access region 134 that is accessible via the open top end 116, the channel 120, and the sidewall opening 124, as described in more detail elsewhere herein. The connection interface assembly 100 includes a locking mechanism 136 disposed within the cavity 112 of the handle 102. In some implementations, the locking mechanism 136 is movable between a projected position 138 (e.g., as shown in FIG. 1C) and a retracted position 140 (e.g., as shown in FIG. 1D). When the locking mechanism 136 is in the projected position 138, the locking mechanism 136 extends into the interface access region 134. When the locking mechanism 136 is in the retracted position 140, the locking mechanism 136 is retracted from extending into the interface access region 134. In some implementations, the locking mechanism 136 includes a biasing element 142 (e.g., a spring coupled to the handle 102 within the cavity 112) that biases the locking mechanism 136 in a normal projected position 138.

The implant removal tool 106 includes a first end 144 and a second end 146. The second end 146 forms a locking interface element 154. The implant removal tool 106 is selectively engageable with the connection interface 104 via an engagement of the locking mechanism 136 with the locking interface element 154 (e.g., when the locking mechanism 136 is in the projected position 138) and via a disengagement of the locking mechanism 136 from the locking interface element 154 (e.g., when the locking mechanism 136 is in the retracted position 140). In some implementations, the implant removal tool 106 is a lateral tool.

The connection interface assembly 100 includes a releasing mechanism 148 that is operatively coupled to the locking mechanism 136. The releasing mechanism 148 may be configured to apply a force to the locking mechanism 136 that causes the locking mechanism 136 to move from the projected position 138 to the retracted position 140. Accordingly, for example, the releasing mechanism 148 may be movable between a first position corresponding to the projected position 138 of the locking mechanism 136 (e.g., as shown in FIG. 1C) and a second position corresponding to the retracted position 140 of the locking mechanism 136 (e.g., as shown in FIG. 1D). The releasing mechanism 148 defines a viewport 152 that provides access to the locking mechanism 136 within the cavity 112 (e.g., which enables a surgeon to view movements associated with the locking mechanism 136, among other examples).

Figure 1H:
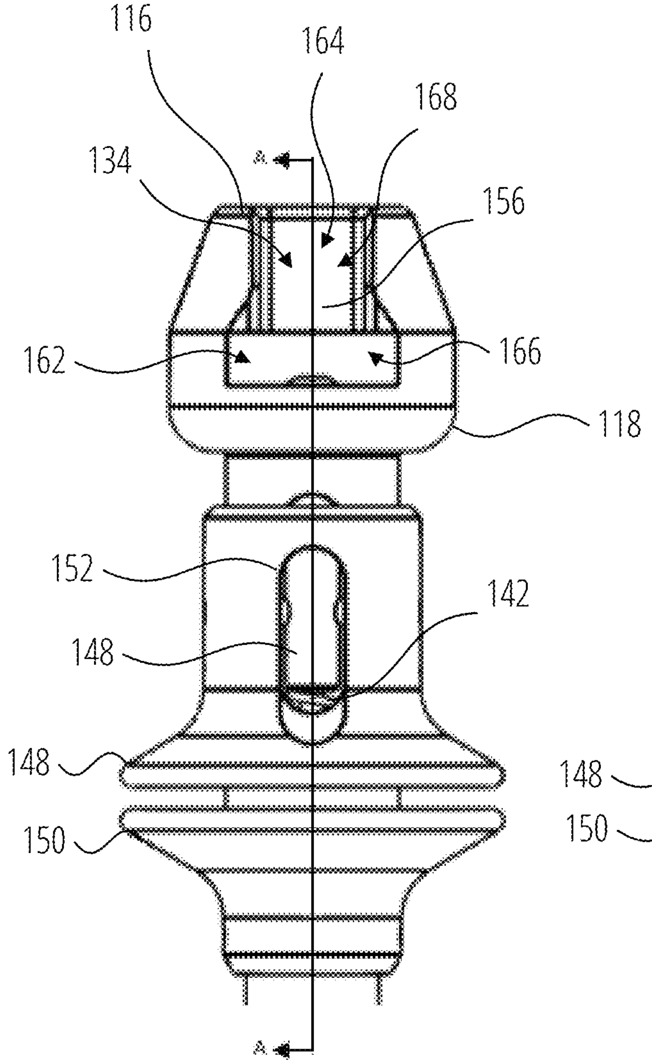
FIG. 1H is a partial side view of an example connection interface assembly including a viewport of a release mechanism, in accordance with some embodiments of the present disclosure.
Figure 1I:
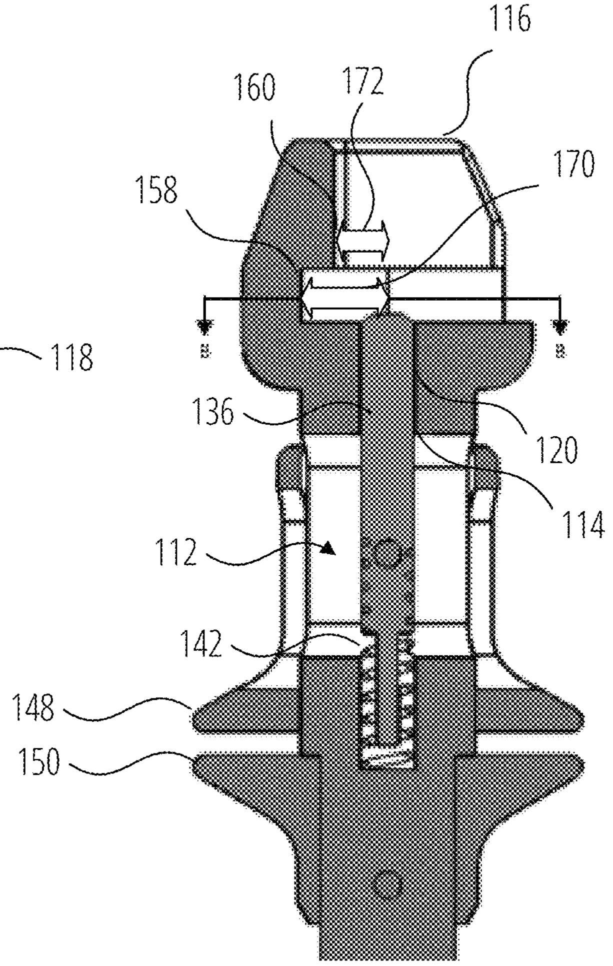
FIG. 1I is a cross-section view taken along line A-A of FIG. 1H, in accordance with some embodiments of the present disclosure.
Figure 1J:
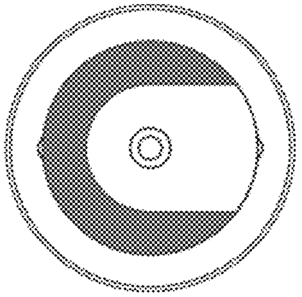
FIG. 1J is a cross-section view taken along line B-B of FIG. 1H, in accordance with some embodiments of the present disclosure.

The connection interface assembly 100 includes a stopping mechanism 150 coupled to the handle 102 proximate the releasing mechanism 148 (e.g., which may be used by the surgeon for leverage when applying a force to the releasing mechanism 148). The sidewall 122 further includes an inner sidewall surface 156 that extends toward the open top end 116. In some implementations, the sidewall inner sidewall surface 156 includes a first inner sidewall surface 156 and a second inner sidewall surface 160 (e.g., as shown in FIG. 1I). The first inner sidewall surface 158 defines a first interface access region 162 and a first sidewall opening 166 (e.g., as shown in FIGS. 1H and 1I). The first sidewall opening 166 has a first width (e.g., a width that corresponds to the first width 132). The first sidewall opening 166 provides access to the first interface access region 162. The second inner sidewall surface 160 defines a second interface access region 164 and a second sidewall opening 168. The second sidewall opening 168 has a second width (e.g., a width that corresponds to the second width 128 and that is less than the first width). The second sidewall opening 168 provides access to the second interface access region 164.

The first inner sidewall surface 158 is concentric about the channel 120 and has a first radius 170 that extends from the first inner sidewall surface 158 to a center point of the channel 120. The second inner sidewall surface 160 is concentric about the channel 120 and has a second radius 172 that extends from the second inner sidewall surface 160 to the center point of the channel 120 (e.g., as shown in FIG. 1I, the first radius 170 is greater than the second radius 172). In some implementations, the locking interface element 154 includes a first portion 174 and a second portion 176 (e.g., as shown in FIG. 1E).

The first portion 174 is cylindrical in cross-section and may include a void having an interior surface. The second portion 176 is rectangular in cross-section and extends in a direction away from the first portion 174. The first portion 174 may have a shape that is complementary in shape to a shape of the first interface access region 162 and the second portion 176 may have a shape that is complementary to a shape of the second interface access region 164. The first interface access region 162 is configured to receive the first portion 174 of the locking interface element 154 and the second interface access region 164 is configured to receive the second portion 176 of the locking interface element 154.

For example, when the locking mechanism 136 is in the normal projected position, the locking mechanism 136 projects into the first interface access region 162. The releasing mechanism 148 may apply a force (e.g., the surgeon may cause the releasing mechanism 148 to move in a direction toward the proximal end 108) to the locking mechanism 136 that causes the locking mechanism 136 to move to the retracted position. The implant removal tool 106 may be inserted (e.g., by the surgeon moving the implant removal tool 106 in a direction that is perpendicular to the movement of the locking mechanism 136) such that the first portion 174 is received in the first interface access region 162 and the second portion 176 is received in the second interface access region 164.

Figure 2:
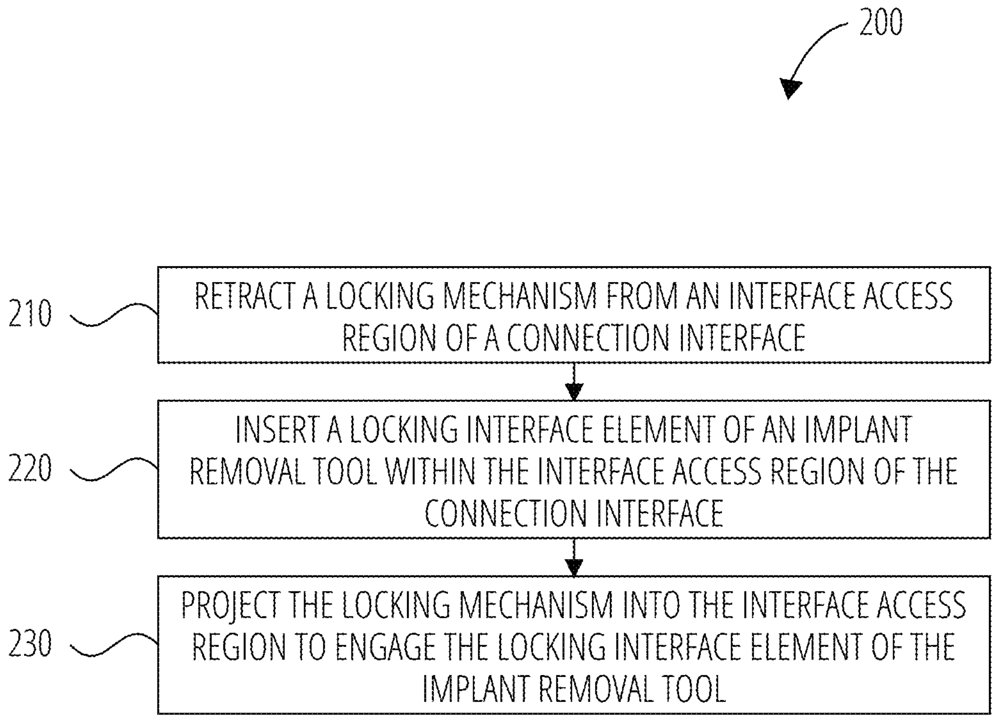
FIG. 2 is a flowchart of an example process associated with connecting an implant removal tool to a connection interface coupled to a handle, in accordance with some embodiments of the present disclosure.

FIG. 2 is a flowchart of an example process 200 associated with connecting an implant removal tool (e.g., the implant removal tool 106) to a connection interface (e.g., the connection interface 104) coupled to a handle (e.g., the handle 102). As shown in FIG. 2, process 200 may include retracting a locking mechanism from an interface access region of a connection interface (block 210). In some implementations, retracting the locking mechanism from the interface access region of the connection interface may include causing a releasing mechanism, operatively coupled to the locking mechanism, to apply a force to the locking mechanism that causes the locking mechanism to retract from the interface access region.

As further shown in FIG. 2, process 200 may include inserting a locking interface element of an implant removal tool within the interface access region of the connection interface (block 220). In some implementations, inserting the locking interface element of the implant removal tool within the interface access region of the connection interface may include moving the locking interface element through a gap that is in communication with the interface access region in a direction that is perpendicular to movement of the locking mechanism between the projected position and the retracted position.

As further shown in FIG. 2, process 200 may include projecting the locking mechanism into the interface access region to engage the locking interface element of the implant removal tool (block 230). In some implementations, the locking mechanism may be projected into the interface access region via a biasing element configured to be coupled to the handle within a cavity of the handle. In some implementations, the interface access region may extend from a bottom portion of the connection interface to an open end of the connection interface. In some implementations, the implant removal tool may be a lateral tool.

Although FIG. 2 shows example blocks of process 200, in some implementations, process 200 may include additional blocks, fewer blocks, different blocks, or differently arranged blocks than those depicted in FIG. 2. Additionally, or alternatively, two or more of the blocks of process 200 may be performed in parallel. The process 200 is an example of one process that may be performed in accordance with the present disclosure. Moreover, while the process 200 has been described in relation to the devices and components of the preceding figures, the process 200 can be performed using alternative, additional, or fewer devices and/or components. Thus, the process 200 is not limited to being performed with the example devices, and/or components explicitly enumerated in the preceding figures.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

When "a processor" or "one or more processors" (or another device or component, such as "a controller" or "one or more controllers") is described or claimed (within a single claim or across multiple claims) as performing multiple operations or being configured to perform multiple operations, this language is intended to broadly cover a variety of processor architectures and environments. For example, unless explicitly claimed otherwise (e.g., via the use of "first processor" and "second processor" or other language that differentiates processors in the claims), this language is intended to cover a single processor performing or being configured to perform all of the operations, a group of processors collectively performing or being configured to perform all of the operations, a first processor performing or being configured to perform a first operation and a second processor performing or being configured to perform a second operation, or any combination of processors performing or being configured to perform the operations. For example, when a claim has the form "one or more processors configured to: perform X; perform Y; and perform Z," that claim should be interpreted to mean "one or more processors configured to perform X; one or more (possibly different) processors configured to perform Y; and one or more (also possibly different) processors configured to perform Z."

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

In the preceding specification, various example embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A connection interface assembly, comprising:

a handle including a proximal end, a distal end, and a cavity including an interior surface, the distal end defining a distal end opening that is in communication with the cavity;

a connection interface including an open top end opposing a bottom portion, the bottom portion being connected to the handle at the distal end and defining a channel that is in communication with the distal end opening, the connection interface including a sidewall extending from the bottom portion to the open top end, the sidewall defining a sidewall opening, the sidewall including an inner sidewall surface, the inner sidewall surface and the bottom portion defining an interface access region that is accessible via the channel, the open top end, and the sidewall opening;

a locking pin disposed within the cavity of the handle, the locking pin being movable between a projected position where the locking pin extends into the interface access region and a retracted position where the locking pin is retracted from extending into the interface access region; and an implant removal tool including a first end and a second end, the second end forming a locking interface, the implant removal tool being selectively engageable with the connection interface via an engagement of the locking pin with the locking interface when the locking pin is in the projected position and a disengagement of the locking pin from the locking interface pin when the locking pin is in the retracted position.

2. The connection interface assembly of claim 1, further comprising:

a release, operatively coupled to the locking pin, configured to apply a force to the locking pin that causes the locking pin to move from the projected position to the retracted position.

3. The connection interface assembly of claim 2, further comprising:

a stop coupled to the handle proximate the release.

4. The connection interface assembly of claim 1, wherein the inner sidewall surface tapers toward the open top end.

5. The connection interface assembly of claim 1, wherein the sidewall opening includes a top having a first width and a bottom having a second width, the second width being greater than the first width.

6. The connection interface assembly of claim 1, wherein the locking pin includes a spring that biases the locking pin into the projected position.

7. The connection interface assembly of claim 1, wherein the implant removal tool is a lateral tool.

8. A connection interface , comprising:

an open top end opposing a bottom portion, the bottom portion defining a channel configured to be in communication with a cavity of a handle;

a sidewall extending from the bottom portion to the open top end, the sidewall including a first inner sidewall surface and a second inner sidewall surface, the first inner sidewall surface defining a first interface access region and a first gap, having a first width, that provides access to the first interface access region, the second inner sidewall surface defining a second interface access region and a second gap, having a second width that is less than the first width, that provides access to the second interface access region, the first interface access region being configured to receive a first portion of an implant removal tool, the second interface access region being configured to receive a second portion of the implant removal tool; and a locking pin movable between a projected position where the locking pin extends into the first interface access region and a retracted position where the locking pin is retracted from extending into the first interface access region, the locking pin configured to engage a locking interface of the first portion of the implant removal tool when the locking pin is in the projected position and configured to disengage the locking pin from the locking interface when the locking pin moves from the projected position to the retracted position.

9. The connection interface of claim 8, wherein the first inner sidewall surface is concentric about the channel and has a first radius, and wherein the second inner sidewall is concentric about the channel and has a second radius that is smaller than the first radius.

10. The connection interface of claim 8, further comprising:

a release, operatively coupled to the locking pin, movable between a first position corresponding to the projected position of the locking pin and a second position corresponding to the retracted position of the locking pin.

11. The connection interface of claim 8, wherein a release defines a viewport that provides access to the locking pin.

12. The connection interface of claim 8, wherein the locking pin includes a spring that biases the locking pin in a normal projected position, the spring being configured to be coupled to the handle within the cavity of the handle.

13. The connection interface of claim 8, wherein the open top end is substantially U-shaped.

14. The connection interface of claim 8, wherein the implant removal tool is a lateral tool.

15. A method for connecting an implant removal tool to a handle via the connection interface recited in claim 8, comprising:

retracting the locking pin from the first interface access region of the connection interface;

inserting a locking interface of the implant removal tool within the first interface access region of the connection interface and projecting the locking pin into the first interface access region to engage the locking interface of the implant removal tool.

16. The method of claim 15, wherein inserting the locking interface of the implant removal tool within the interface access region of the connection interface comprises:

moving the locking interface through a gap that is in communication with the interface access region in a direction that is perpendicular to movement of the locking pin between the projected position and the retracted position.

17. The method of claim 15, wherein the locking pin is projected into the interface access region via a spring configured to be coupled to the handle within a cavity of the handle.

18. The method of claim 15, wherein retracting the locking pin from the interface access region of the connection interface comprises:

causing a release, operatively coupled to the locking pin , to apply a force to the locking pin that causes the locking pin to retract from the interface access region.

19. The method of claim 15, wherein the interface access region extends from a bottom portion of the connection interface to an open end of the connection interface.

20. The method of claim 15, wherein the implant removal tool is a lateral tool.

* * * * *